(12) United States Patent
Lee et al.

(10) Patent No.: US 7,011,651 B2
(45) Date of Patent: Mar. 14, 2006

(54) DEVICE FOR REGULATING FLOW RATE OF INTRAVENOUS MEDICAL SOLUTION DURING INJECTION

(75) Inventors: Sang Bin Lee, Seoul (KR); Ho Gil Chu, Kyunggi-do (KR); Hyung Jin Sung, Daejeon (KR)

(73) Assignee: Meinntech Co., Ltd, (KR)

( * ) Notice: Subject to any disclaimer, the term of this patent is extended or adjusted under 35 U.S.C. 154(b) by 61 days.

(21) Appl. No.: 10/497,265

(22) PCT Filed: Nov. 28, 2002

(86) PCT No.: PCT/KR02/02233

§ 371 (c)(1),
(2), (4) Date: May 27, 2004

(87) PCT Pub. No.: WO03/045475

PCT Pub. Date: Jun. 5, 2003

(65) Prior Publication Data

US 2005/0065480 A1    Mar. 24, 2005

(30) Foreign Application Priority Data

Nov. 29, 2001   (KR) ...................... 10-2001-0074845

(51) Int. Cl.
*A61M 5/00* (2006.01)
(52) U.S. Cl. ...................... 604/251; 604/246; 251/149; 251/149.5; 251/160
(58) Field of Classification Search ............... 604/30, 604/32, 118, 186, 246, 248, 251–255; 251/84, 251/142, 149, 149.1, 149.2, 149.5, 153, 160, 251/284–288

See application file for complete search history.

(56) References Cited

U.S. PATENT DOCUMENTS

| 4,515,588 | A | * | 5/1985 | Amendolia | 604/118 |
| 4,802,506 | A | * | 2/1989 | Aslanian | 137/556 |
| 5,005,604 | A | * | 4/1991 | Aslanian | 137/556 |
| 6,195,012 | B1 | * | 2/2001 | Yang | 340/618 |
| 6,213,986 | B1 | * | 4/2001 | Darling, Jr. | 604/248 |
| 2003/0135164 | A1 | * | 7/2003 | Simon | 604/246 |

* cited by examiner

*Primary Examiner*—Cris Rodriguez
(74) *Attorney, Agent, or Firm*—Martine Penilla & Gencarella, LLP

(57) ABSTRACT

The object of this invention is to provide a device for regulating the flow rate of an intravenous medical solution during an injection using an intravenous drip unit. The device has a housing (10) mounted to a hose (300) to allow the flow of the solution from a solution container (200) into the vein, and a control member (20) rotatably assembled with the housing to regulate the flow rate of the solution. The housing has first and second seats (11, 12) communicating with inlet and outlet ports, and the control member has first and second bosses (21, 22) seated in the first and second seats. An arc-shaped solution path (23), a radial channel (24) and an annular groove (25) are formed on the control member to regulate the flow rate of the solution in accordance with an adjusted angle of the control member relative to the fixed housing.

7 Claims, 5 Drawing Sheets

DEVICE FOR REGULATING FLOW RATE OF INTRAVENOUS MEDICAL SOLUTION DURING INJECTION

TECHNICAL FIELD

The present invention relates, in general, to devices for regulating the flow rate of an intravenous medical solution which are used for regulating the flow rate of the medical solution during injection of the solution, for example, Ringer's solution, specifically prepared liquid medicines, or other injectable solutions, into a vein of a patient and, more particularly, to a device for regulating the flow rate of an intravenous medical solution during an injection, which has a controllable path capable of allowing a user to finely regulate the flow rate of the medical solution.

BACKGROUND ART

Some patients are impaired in their gastroenteric functions to have poor digestion, so it is sometimes necessary to inject intravenous medical solutions such as dextrose solutions, specifically prepared liquid medicines, or other injectable solutions contained in solution packs or bottles, into a vein of a patient using an intravenous drip unit.

During injection of specific intravenous medical solutions, such as liquid anticancer drugs or liquid antibiotics, into the veins of infant patients or other persons who are seriously ill, it is necessary to continuously inject the solutions into the veins at constant flow rates determined in accordance with the physical conditions of the patients.

When the injection of specific medical solutions into the veins is performed while failing to continuously inject the solution into a vein at a constant flow rate determined in accordance with the physical condition of a patient, there is a danger of shock or injury to the patient due to incorrectly supplied dosage of he medical solution.

An intravenous drip unit, or a so-called "clamp", which has been used in injection of an intravenous medical solution, for example, Ringer's solution, specifically prepared liquid medicines, or other injectable solutions, into a vein of the patient, typically comprises a solution container containing the medical solution, a hose hermetically extending from the lower end of the container to a predetermined length, a solution flow confirming member mounted to an intermediate position of the hose to allow a user to confirm the flow rate of the solution, a needle mounted to the outside end of the hose so as to inject the solution into the vein, and a solution flow regulator mounted to the hose at a position between the solution flow confirming member and the needle to allow the user to regulate the flow rate of the solution flowing to the needle as desired.

In order to inject a medical solution into a vein of a patient using such an intravenous drip unit, a user, for example, a nurse, inserts the needle of the drip unit into the vein, and controls the solution flow regulator to regulate the flow rate of the solution in the hose, thus allowing the solution to be injected into the vein at the regulated flow rate.

Such a conventional solution flow regulator is typically designed such that a user rotates the regulator upward or downward to control the sectional area of the hose, thus regulating the flow rate of the solution. The hose is typically made of a soft plastic or rubber material, and so the regulator may fail to finely regulate the flow rate of the solution after repeated use over a lengthy period of time.

In addition, several types of solution injectors designed to automatically regulate the flow rate of an intravenous medical solution during an injection have been proposed and widely used for medical applications.

However, such an injector is expensive, and must be used with an additional intravenous drip unit, so that the injectors are inconvenient to users while storing and managing the injectors. Another problem of the injectors resides in that they often malfunction and are easily broken, so that the injectors may unexpectedly stop injection of a solution into a vein, or inject the solution into the vein at an excessive flow rate, or forcibly inject the solution into the vein to cause a danger of shock or injury to the patients.

DISCLOSURE OF THE INVENTION

Accordingly, the present invention has been made keeping in mind the above problems occurring in the prior art, and an object of the present invention is to provide a device for regulating the flow rate of an intravenous medical solution, for example, Ringer's solution, specifically prepared liquid medicines, or other injectable solutions, during an injection using an intravenous drip unit, which continuously injects the solution into a vein of the patient at a constant flow rate determined in accordance with the physical conditions of the patient, thus naturally and effectively injecting the solution into the vein, and thereby optimizing the effect of the solution upon the patient's body, and which allows a user to finely regulate the flow rate of the solution during the injection, thus almost completely preventing medical hazards caused by injection of a deficient or excessive amount of medical solution into the vein, and thereby enhancing safety during an intravenous injection.

In order to accomplish the above object, the present invention provides a device for regulating the flow rate of an intravenous medical solution, such as Ringer's solution, specifically prepared liquid medicines, or other injectable solutions, during injection of the solution into a vein of a patient using an intravenous drip unit having a solution container containing the medical solution, a hose extending from the lower end of the container to a predetermined length, and a needle mounted to the outside end of the hose so as to inject the medical solution into the vein of the patient, wherein the device comprises a housing mounted to an intermediate portion of the hose and having a solution path to allow the flow of the solution from the solution container into the vein, and a control member rotatably assembled with the housing to regulate the flow rate of the solution.

The housing has a stepped depression on a side thereof, with first and second seats formed in the stepped depression to allow the medical solution to controllably flow through the housing. The housing also has an inlet port communicating with the first seat, and an outlet port communicating with the second seat, with a locking hole formed on the center of an end wall of the housing to assemble the control member with the housing.

The control member has a stepped boss part on a side thereof, with first and second bosses formed by the stepped boss part and seated in the first and second seats of the housing, respectively. An arc-shaped solution path is formed on an annular end surface of the first boss within an angular range of about 320°~355°. A radial channel is formed on the annular end surface of the first boss such that the channel communicates with an end surface of the second boss. An annular groove is formed on the end surface of the second boss of the control member to communicate with the radial channel. A locking hub is formed at the center of the end surface of the second boss to engage with the locking hole of the housing, with a locking hook formed around the outside end of the locking hub to be seated against the outside surface of the housing when assembling the control member with the housing.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
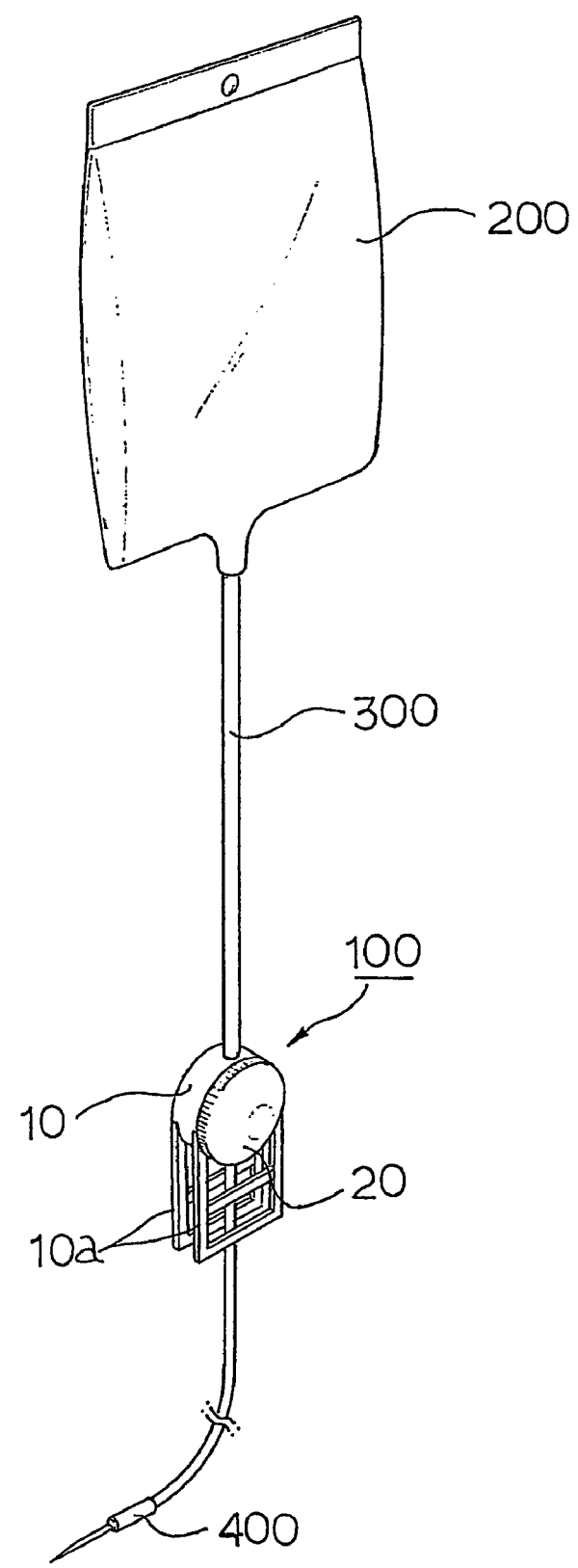
FIG. 1 is a perspective view of an intravenous drip unit equipped with a device for regulating the flow rate of an intravenous medical solution during an injection in accordance with a preferred embodiment of the present invention.

Reference should now be made to the drawings, in which the same reference numerals are used throughout the different drawings to designate the same or similar components.

FIG. 1 is a perspective view of an intravenous drip unit equipped with a device for regulating the flow rate of an intravenous medical solution during an injection in accordance with a preferred embodiment of the present invention.

Figure 2:
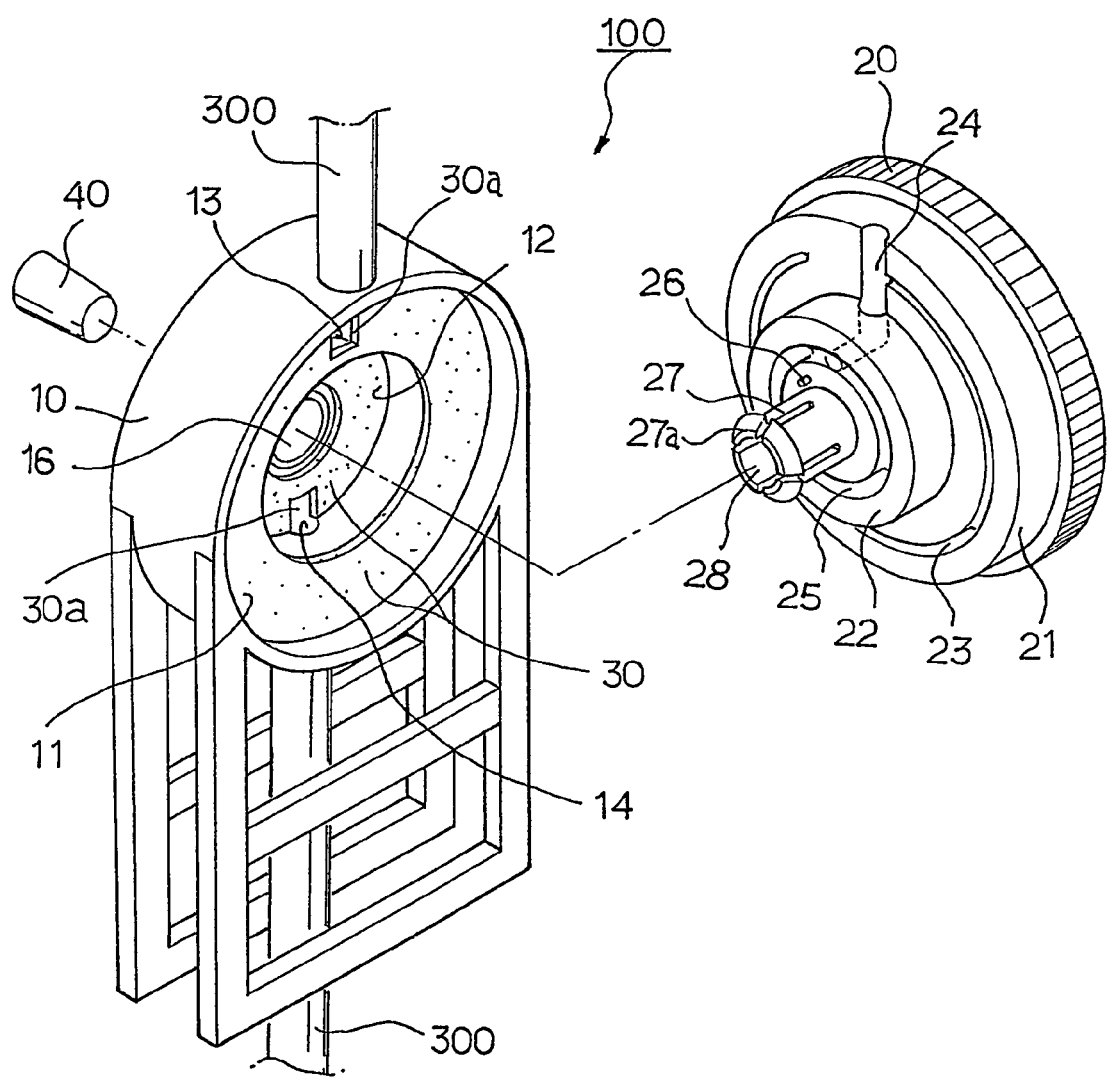
FIG. 2 is an exploded perspective view of the regulating device according to the present invention.
Figure 3:
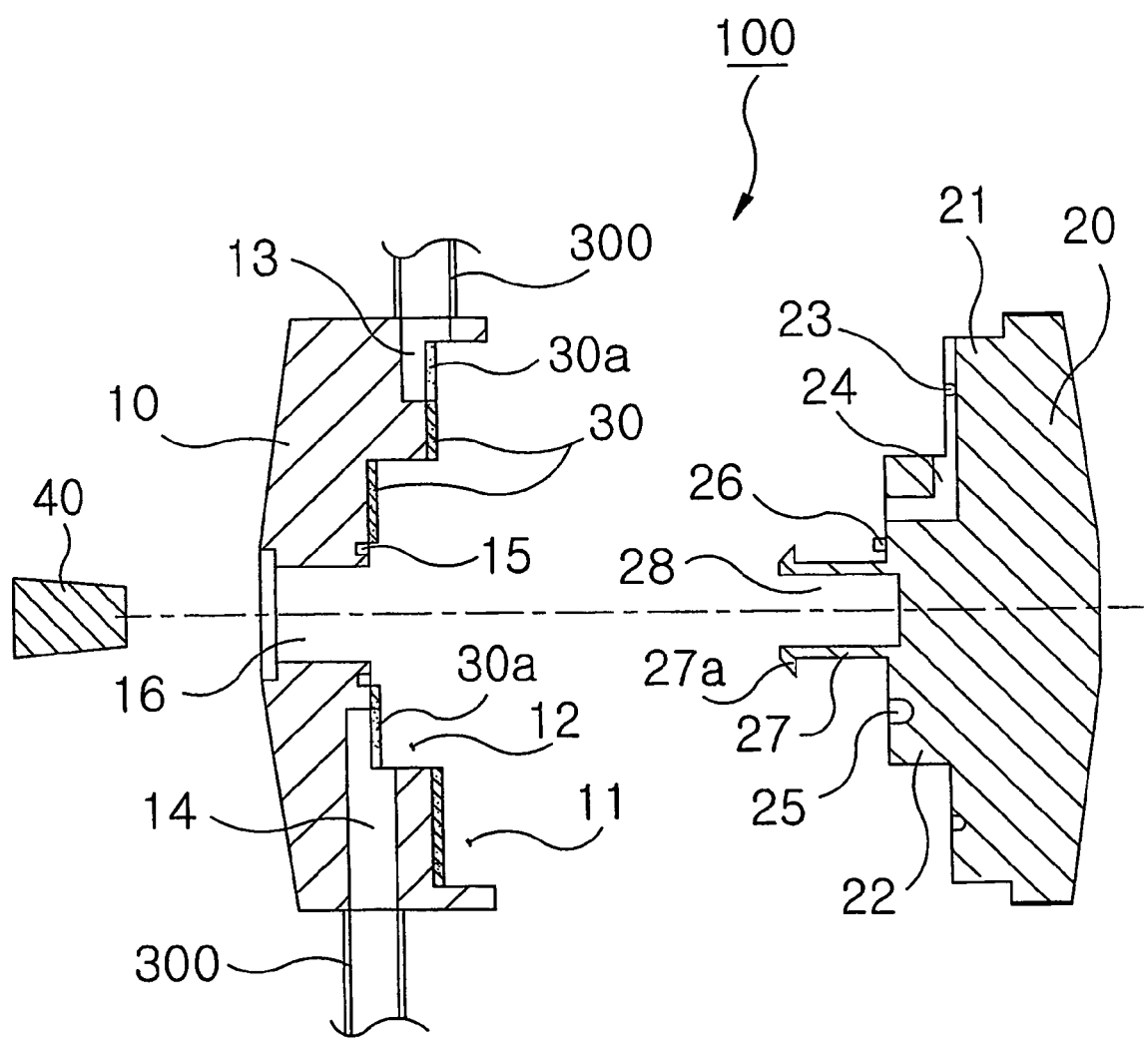
FIG. 3 is a sectional view of the regulating device according to the present invention, before the parts of the device have been assembled into a single body.

FIG. 2 is an exploded perspective view of the regulating device. FIG. 3 is a sectional view of the regulating device before the parts of the device are assembled into a single body.

As shown in the drawings, an intravenous drip unit, preferably used with the regulating device 100 of the invention, includes a solution container containing an intravenous medical solution such as Ringer's solution, specifically prepared liquid medicines, or other injectable solutions. In the preferred embodiment, a solution pack 200 is used as the solution container, but it should be understood that a solution bottle in place of such a solution pack 200 may be used as the solution container. A hose 300 hermetically extends from a lower end of the solution pack 200 to a predetermined length, and a needle 400 is mounted to an outside end of the hose 300 so as to inject the medical solution into a vein of the patient. The regulating device 100 of the present invention is mounted to an intermediate portion of the hose 300, and regulates the flow rate of the medical solution injected into the vein of the patient during injection of the solution.

The regulating device 100 includes a fixed housing 10 and a knob-type rotatable control member 20. The housing 10 is fixedly mounted to a predetermined intermediate portion of the hose 300 and guides the flow of the medical solution from the pack 200 into the vein of the patient. The knob-type control member 20 is rotatably inserted into a side of the housing 10 to regulate the flow rate of the medical solution. A locking member 40 is inserted into the control member 20 after passing through the housing 10, thus mounting the control member 20 to the housing 10 while preventing undesired movement of the control member 20 relative to the housing 10.

The housing 10 has a stepped depression on a side thereof, with first and second seats 11 and 12 formed in the stepped depression to allow the medical solution to controllably flow through the housing 10. The housing 10 also has an inlet port 13 provided at an upper portion of the first seat 11 to communicate with the first seat 11, and an outlet port 14 provided at a lower portion of the second seat 12 to communicate with the second seat 12.

A locking hole 16 is formed on the center of an end wall of the housing 10, thus forming an annular end surface on the second seat 12, with an arc-shaped groove 15 formed on the annular end surface of the second seat 12 within an angular range of about 320°~355° around the locking hole 16.

A hand grip 10a is provided at a lower portion of the housing 10 for allowing a user to rotate the control member 20 with one hand.

The knob-type control member 20, rotatably assembled with the housing 10 to regulate the flow rate of the medical solution, has a stepped boss part on a side thereof, with first and second bosses 21 and 22 formed by the stepped boss part and seated in the first and second seats 11 and 12 of the housing 10, respectively. An arc-shaped solution path 23 is formed on an annular end surface of the first boss 21 within an angular range of about 320°~355°, and a radial channel 24 is formed on the annular end surface of the first boss 21 to communicate with a first end of the solution path 23 and extends into the second boss 22 until the channel 24 communicates with an end surface of the second boss 22.

The arc-shaped solution path 23 of the control member 20 is gradually reduced in a width or depth thereof by 0~0.5 mm in a direction from a second end to the first end of the path 23.

An annular groove 25 is formed on the end surface of the second boss 22 of the control member 20 to communicate with the radial channel 24, and a protrusion 26 is formed on the end surface of the second boss 22 to engage with the arc-shaped groove 15 formed on the annular end surface of the second seat 12 of the housing 10. A locking hub 27 having a predetermined length is formed at the center of the end surface of the second boss 22.

An axial hole 28 is formed in the locking hub 27 to engage with the locking member 40, with a locking hook 27a formed around the outside end of the hollow locking hub 27. The sidewall of the hollow locking hub 27 is axially slit at several positions, thus having elasticity to expand and contract in a radial direction.

A packing member 30, made of rubber, is laid on the annular end surface of each of the first and second seats 11 and 12 to prevent leakage of the medical solution from the device 100 to the outside. A communication hole 30a is formed at a predetermined position of each packing member 30 to communicate with the inlet or outlet port 13 or 14 of the housing 10.

When the knob-type control member 20 is assembled with the housing 10 into a single body, the control member 20 is fully inserted into the housing 10 such that the first and second bosses 21 and 22 of the control member 20 are seated in the first and second seats 11 and 12 of the housing 10, respectively. In such a case, the radially contractible locking hub 27 of the control member 20 is completely inserted into the locking hole 16 of the housing 10, so that the locking hook 27a of the hollow locking hub 27 is projected outside the locking hole 16 to be closely seated against the outside surface of the housing 10. It is thus possible to prevent undesired removal of the control member 20 from the housing 10. The locking member 40 is fully inserted from the outside of the housing 10 into the axial hole 28 of the locking hub 27, thus elastically expanding the locking hub 27 in the radial direction and preventing undesired movement of the control member 20 relative to the housing 10.

In another embodiment (not shown) of the present invention, the annular groove 25 may be formed on the annular end surface of the first boss 21 in place of the second boss 22, and the arc-shaped solution path 23 may be formed on the annular end surface of the second boss 22 in place of the first boss 21 within an angular range of about 320°~355°.

During injection of an intravenous medical solution, the solution flows from the solution pack 200 into the inlet port 13 of the regulating device 100 through the hose 300. When the control member 20 is controlled to cause the radial channel 24 to be directly aligned with the inlet port 13 of the housing 10, the medical solution directly flows from the inlet port 13 into the channel 24, and passes through the annular groove 25, prior to being discharged from the device 100 through the outlet port 14 to be injected into a vein of the patient.

However, when the control member 20 is controlled to cause the second end of the arc-shaped solution path 23 to be aligned with the inlet port 13 of the housing 10, the medical solution flows from the inlet port 13 into the solution path 23, and is introduced into the channel 24 from the first end of the path 23. Thereafter, the medical solution flows along the annular groove 25, prior to being discharged from the device 100 through the outlet port 14 to be injected into the vein of the patient.

Figure 4A:
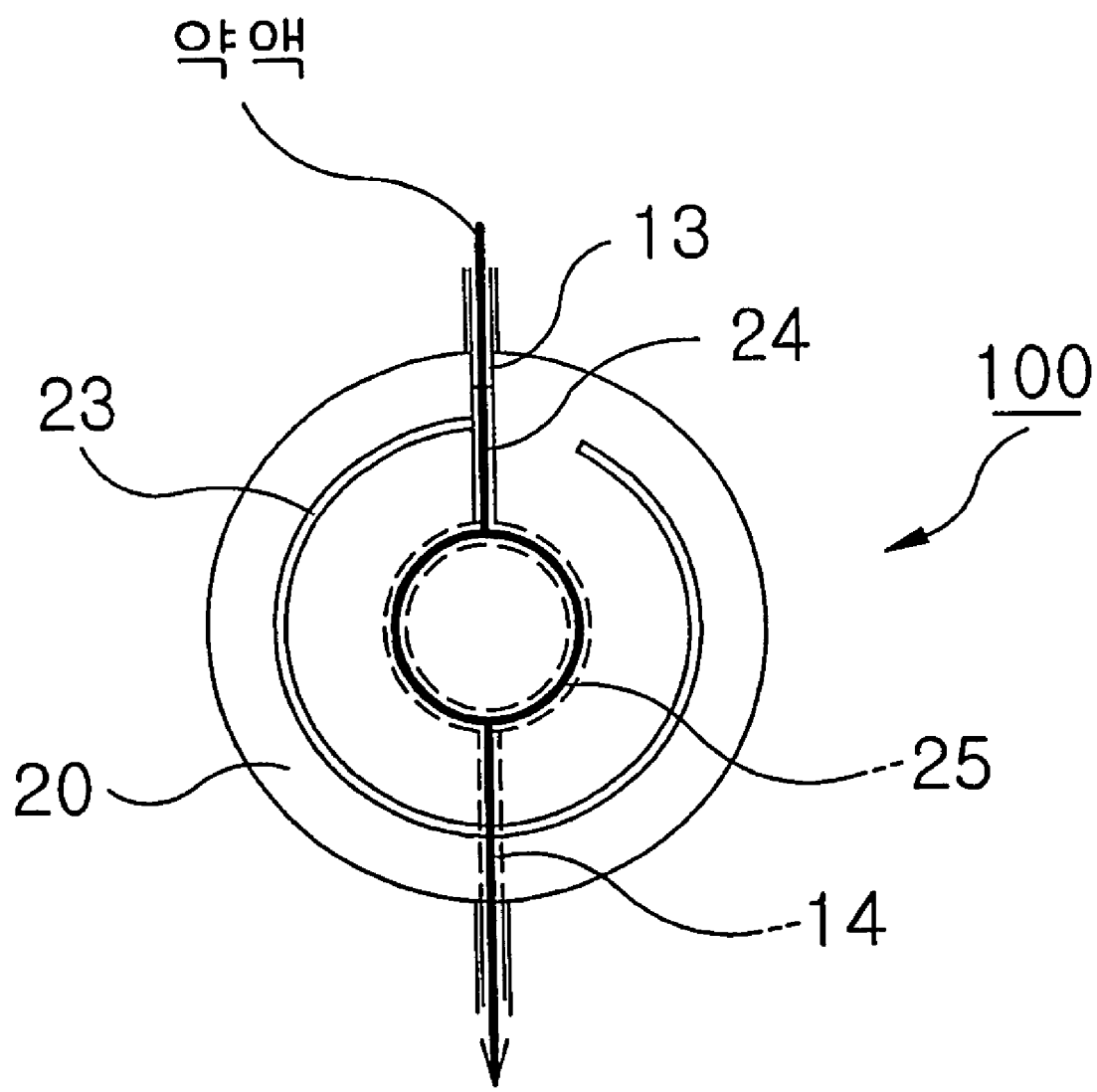
FIG. 4a is a schematic view of the regulating device according to the present invention when the device is adjusted to a high level, at which an intravenous medical solution flows at a high flow rate.

In a detailed description, when the control member 20 is controlled such that the radial channel 24 is directly aligned with the inlet port 13 of the housing 10 as shown in FIG. 4a, the medical solution flows from the inlet port 13 to the outlet port 14 through the channel 24, so that the flow rate of the medical solution in the device 100 is maximized.

Figure 4B:
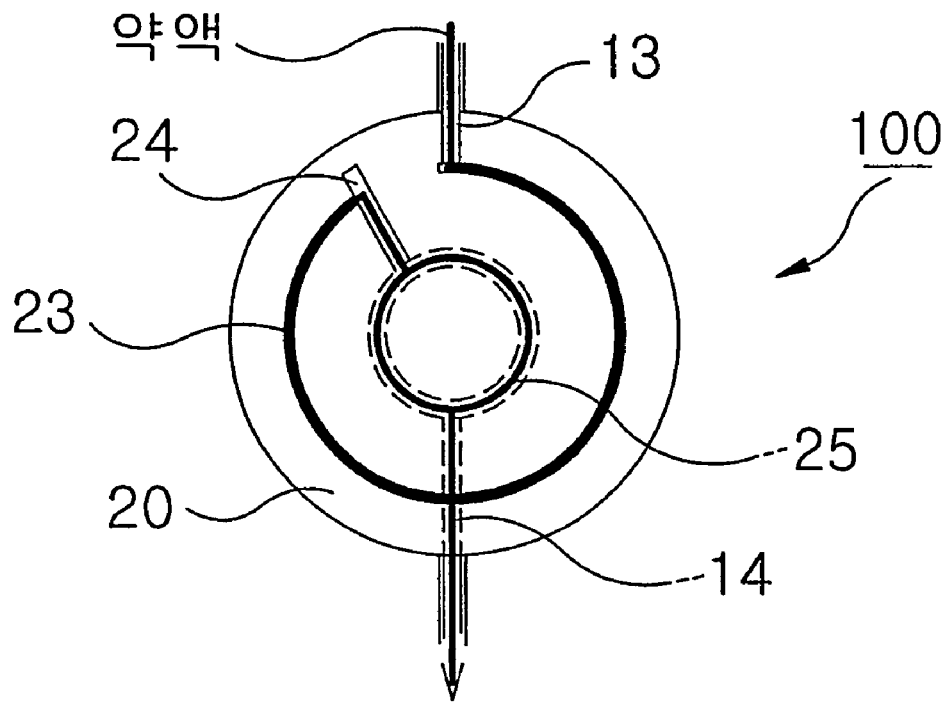
FIG. 4b is a schematic view of the regulating device according to the present invention when the device is adjusted to a low level, at which the medical solution flows at a low flow rate.

In order to reduce the flow rate of the medical solution, the knob-type control member 20 is carefully rotated clockwise relative to the housing 10 from the position of FIG. 4a where the channel 24 is aligned with the inlet port 13 to another position of FIG. 4b. In such a case, the length and width of the solution path 23 are gradually increased, respectively, in a direction away from the inlet port 13, so that the flow rate of the solution injected into the vein is gradually reduced in inverse proportion to an increase in the length of the path 23.

Figure 4C:
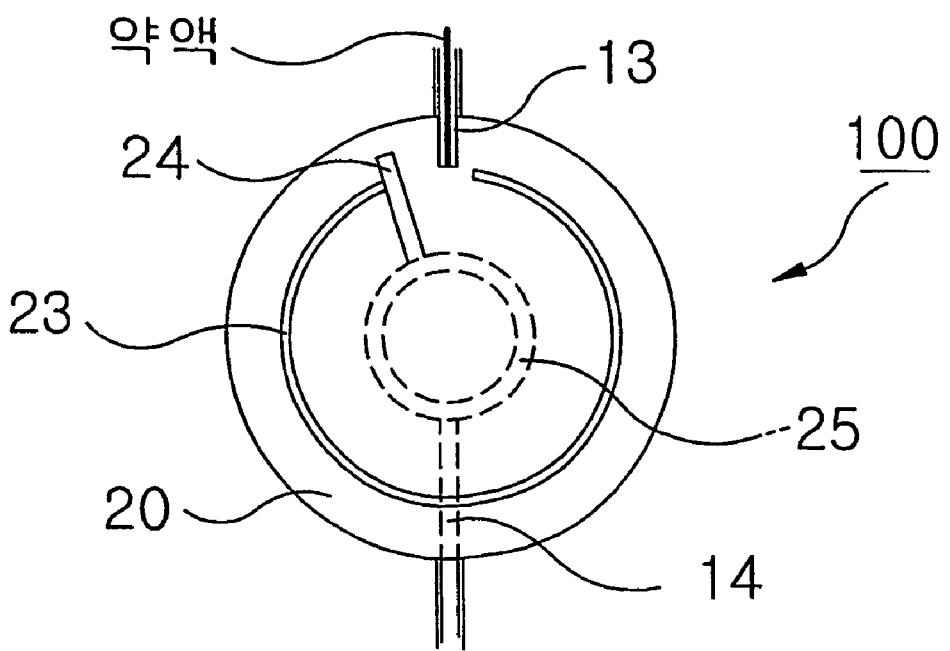
FIG. 4c is a schematic view of the regulating device according to the present invention when the device is adjusted to a neutral position, at which the device does not allow the medical solution to flow.

When the knob-type control member 20 is rotated clockwise relative to the housing 10 at an angle of 320° or more from the position of FIG. 4a where the channel 24 is aligned with the inlet port 13, the device 100 accomplishes a stop position as shown in FIG. 4c. In the stop position, the protrusion 26 of the second boss 22 of the control member 20 is stopped at an end of the arc-shaped groove 15 of the second seat 12 of the housing 10. Therefore, the solution path 23 is disconnected from the inlet port 13, so that the device 100 stops the flow of the solution. The injection of the solution into the vein is thus stopped.

When the knob-type control member 20 is rotated counterclockwise relative to the housing 10 at an angle of 320° from the position of FIG. 4c where the solution path 23 is disconnected from the inlet port 13, the length and width of the solution path 23 are gradually reduced, respectively, in a direction toward the inlet port 13, so that the flow rate of the solution injected into the vein is gradually increased.

In a brief description, the flow rate of the solution injected into the vein is finely regulated in accordance with an angular adjustment of the rotatable control member 20 relative to the fixed housing 10, which results in a fine change in the length of the solution path 23 from the inlet port 13 to the radial channel 24.

In accordance with a further embodiment (not shown) of the present invention, the device 100 may be designed such that the port 14 is connected to an inlet part of the hose 300 extending from the pack 200 to the device 100, and the port 13 is connected to the outlet part of the hose 300 extending from the device 100 to the needle 400. In such a case, the medical solution from the pack 200 primarily flows into the port 14 through the inlet part of the hose 300 and secondarily passes through the annular groove 25 to flow into the radial channel 24. The solution from the radial channel 24 may be directly discharged from the device 100 to the needle 400 through the port 13, or indirectly discharged from the device 100 to the needle 400 through the port 13 after flowing along the path 23.

The regulation of the flow rate of the medical solution in the above-mentioned altered embodiment is performed in the same manner as that described for the embodiment of the drawings.

INDUSTRIAL APPLICABILITY

As described above, the present invention provides a device for regulating the flow rate of an intravenous medical solution, for example, Ringer's solution, specifically prepared liquid medicines, or other injectable solutions, during an injection of the solution into a vein of a patient using an intravenous drip unit. The device regulates the flow rate of the solution by changing the length and width of its solution path, thus finely regulating the flow rate of the solution. This device is thus preferably used by a patient into whose vein a medical solution must be continuously injected at a predetermined constant flow rate. The device also prevents injection of an excessive amount of medical solution into a vein, which may be caused by a conventional solution flow regulator after repeated use over a lengthy period of time. In addition, the device of the present invention may be preferably used, in place of conventional expensive injectors that are inconvenient to users while storing and managing them, and often malfunction to unexpectedly stop injection of a solution into a vein, or inject the solution into the vein at an excessive flow rate, or forcibly inject the solution into the vein to cause a danger of shock or injury to a patient even though the injectors automatically regulate the flow rate of the solution.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A device for regulating a flow rate of an intravenous medical solution, such as Ringer's solution, specifically prepared liquid medicines, or other injectable solutions, during injection of the solution into a vein of a patient using an intravenous drip unit having a solution container containing the medical solution, a hose extending from a lower end of the container to a predetermined length, and a needle mounted to an outside end of said hose so as to inject the medical solution into the vein of the patient, said device comprising:
- a housing mountable to an intermediate portion of said hose, said housing having a stepped depression on a side thereof, with first and second seats formed in the stepped depression to allow the medical solution to controllably flow through the housing, said housing also having an inlet port provided at an upper portion of said first seat to communicate with the first seat, and an outlet port provided at a lower portion of said second seat to communicate with the second seat;
- a control member rotatably assembled with said housing to regulate the flow rate of the medical solution, said control member having a stepped boss part on a side thereof, with first and second bosses formed by the stepped boss part and seated in the first and second seats of the housing, respectively, with an arc-shaped solution path formed on an annular end surface of said first boss within an angular range of about 320°~355°, and a radial channel formed on the annular end surface of the first boss to communicate with a first end of said solution path and extending into the second boss until the channel communicates with an end surface of the second boss; and
- a locking member mounting the control member to the housing while preventing undesired movement of the control member relative to the housing.

2. The device according to claim 1, wherein a locking hole is formed on a center of an end wall of said housing, thus forming an annular end surface on the second seat, with an arc-shaped groove formed on the annular end surface of the second seat within an angular range of about 3200~355° around said locking hole.

3. The device according to claim 1, wherein said arc-shaped solution path of the control member is gradually reduced in a width or depth thereof by 0~0.5 mm in a direction from a second end to the first end of said solution path.

4. The device according to claim 1, wherein an annular groove is formed on the end surface of said second boss of the control member to communicate with the radial channel, and a protrusion is formed on said end surface of the second boss to engage with an arc-shaped groove formed on an annular end surface of the second seat of the housing, and a locking hub is formed at a center of said end surface of the second boss.

5. The device according to claim 4, wherein an axial hole is formed in said locking hub to engage with said locking member, with a locking hook formed around an outside end of said locking hub having the axial hole.

6. The device according to claim 1, wherein a packing member, made of rubber, is laid on an annular end surface of each of said first and second seats to prevent leakage of the medical solution from the device to an outside, with a communication hole formed at a predetermined position of the packing member to communicate with the inlet or outlet port of the housing.

7. The device according to claim 1, wherein a hand grip is provided at a lower portion of the housing to allow a user to rotate the control member with one hand.

* * * * *